United States Patent [19]

Shah et al.

[11] Patent Number: 5,294,437
[45] Date of Patent: Mar. 15, 1994

[54] HAIR SPRAY

[75] Inventors: Snehal M. Shah, Artesia; Candelario A. Fernandez, Jr., Torrance, both of Calif.

[73] Assignee: Neutrogena Corporation, Los Angeles, Calif.

[21] Appl. No.: 975,787

[22] Filed: Nov. 13, 1992

[51] Int. Cl.⁵ .......................... A61K 7/09; A61K 7/11
[52] U.S. Cl. ........................................ 424/71; 424/41; 424/70; 424/DIG. 1; 424/DIG. 2
[58] Field of Search .............. 424/47, 70, 71, DIG. 1, 424/DIG. 2

[56] References Cited

U.S. PATENT DOCUMENTS

| | | | |
|---|---|---|---|
| 4,543,249 | 9/1985 | Netson | 424/70 |
| 4,983,377 | 1/1991 | Murphy et al. | 424/47 |

*Primary Examiner*—Thurman K. Page
*Assistant Examiner*—Jyothsna Venkat
*Attorney, Agent, or Firm*—Richard R. Mybeck

[57] ABSTRACT

A hair spray composition exhibiting high curl retention, fast drying time, high rinse-out with low flaking and high shine characteristics comprised of fixative resins, silicone plasticizers and neutralizers in a crystal clear formulation which meets or exceeds the currently mandated alcohol requirements in a hand pump spray application.

1 Claim, No Drawings

HAIR SPRAY

INTRODUCTION

The present invention relates generally to personal care products and grooming aids and more particularly to a new and novel pumpable hair spray composition containing preselected resins, neutralizers and silicone blends in a mixture with an water/alcohol solvent vehicle and which, when applied as a spray mist to human hair provides a surprisingly effective hair control product while substantially reducing the ecological detriment of prior art products.

BACKGROUND OF THE INVENTION

In the preparation of prior art aerosol and pump spray hair care formulations, pure (100%) alcohol has, heretofore, been the primary solvent of choice utilized in consumer "pump" hair sprays to deliver the product onto human hair for hair control and cosmetic appearance. Discussions of such products appear in *Cosmetics: Science and Technology*, Balsam and Sagarin, 2nd Ed., Vol. 2, 352–358, and *Hair and Hair Products*, Society of Cosmetic Chemists Continuing Education Program (held in Los Angeles, Calif., Feb. 3–4, 1992) which are incorporated herein by this reference hereto.

Hair spray is a styling and beautifying aid used by 65% of women over thirteen. Seventy percent of these women use hair spray daily. Consumers require hair sprays to perform in holding their hairstyle and also to contribute to beautifying the appearance of their hair. People who perm and color their hair are also concerned that the hair spray will not dull the color of their hair or weigh down their curls. Consumers are also conscious of environmental issues and expect their products to comply with regulations without sacrificing performance.

Good holding power is perhaps the primary attribute a consumer looks for in a hair spray. Curl retention under conditions of changing humidity, especially changes to a higher humidity, is critical to the performance of a hair spray. Good curl retention in chemically damaged hair is important since the hair fiber is weakened by the chemical process and will be less likely to maintain the curl. In addition, the hair spray must be capable of being washed out of the hair with shampoo and it must not build up on the hair over successive use. The consumer also requires the hair spray to perform as a beautifying agent. It is expected to contribute positively to the appearance of the hair. Improved shine and luster are some properties a consumer expects. Therefore, a careful equilibrium between ingredients must exist to provide superior hold, be rinsable without buildup, non-flaking, and yet provide shine and manageability.

Hair sprays are similar in their basic ingredient content. They contain solvents, a synthetic polymeric resin, a base to neutralize the resin (especially when the resin is a carboxylic acid containing resin), plasticizers and in some cases a surfactant and a fragrance. The resin is the primary ingredient responsible for the curl retention characteristics. The neutralizer contributes to the resin's film properties and also to the resin's solubility or wash out property. Surfactants improve the spreadability of the resin on the hair surface. Plasticizers are added to provide less brittle films, minimize flaking and to maximize shine and curl retention. Hair sprays differ from each other by the type of resin(s) and neutralizer used, the degree of neutralization of the resin, and the use of various types of plasticizers and surfactants. The blending of these ingredients is important in order to obtain and maximize desired properties in the consumer product.

Three types of hair sprays are on the market today; pump hair sprays, hydrocarbon aerosols and carbon dioxide aerosols. Pump hair sprays and hydrocarbon aerosols comprise the majority of the market sales. The predominant solvent system in all three types of hair sprays is alcohol. New regulations require the alcohol level to be limited to a maximum content of 80% in current and new products in an effort to reduce volatile organic compounds (VOC's) at ground level which form ozone through a photochemical reaction with nitrogen oxides in the presence of sunlight.

In response to consumer and environmental needs, we have developed three pump hair sprays that fulfill consumers high expectations in performance while meeting strict standards for reduced air pollution.

Active ingredients found in the prior art hair spray formulations include: a fixative resin such as octyl acrylamide/acrylates copolymer octylacrylamide/acrylates/butylaminoethyl methacrylate copolymer and the like; neutralizing agents, especially desirable when the fixative resin is an acrylic acid, such as sodium hydroxide, aminomethylpropanol (AMP), triethanolamine and the like; solvents including water and alcohols; propellants such as hydrocarbons and the like for aerosol products; plasticizers such as dimethyl silicone, triethyl citrate and lanolin derivatives; and other optional ingredients such as perfumes, coloring agents and pH adjusters depending on the properties desired in a final formulation.

Given that silicones in a synergistic combination with other specially preselected ingredients is a salient feature of the present invention, and that silicones have been employed in prior art hair sprays, it is essential to understand the diverse roles such compounds may play in the hair spray art. A key review of this aspect of the art is found in *Hair Fixatives—benefit from the physical and chemical properties of silicones*. Christine M. Handt, *Soap/Cosmetics Soecialties*. October 1987 wherein is reported that different silicones, in diverse concentrations can provide a variety of benefits to hair fixative systems, including softer feel, shine and better curl retention.

The "pump" hair spray products of the prior art contain 100% alcohol as the solvent/carrier. However, this can no longer be. standards require that the alcohol content of such products cannot exceed 80% beginning Jan. 1, 1993 (See: Product Standards for Hair Sprays, California Clean Air Act).

Many researchers are engaged in the hunt for a replacement formulations of pump hair sprays which will be environmentally safe and yet functionally acceptable to the consuming public. However, problems arise when water is used to either replace alcohol or to reduce the alcohol to the mandated content of less than 80%. Because the products created thus far leave hair flat and dull, require excessive drying time, promote increased tackiness and exhibit substantially weaker holding power for curls.

Obviously, the problems involved in adding relatively small amounts of water, approximately 15% of the solvent system, to a pump hair spray are very significant. The reason is that water greatly affects the physical properties of the fixatives.

The ultimate product, heretofore unattainable, should provide: a hair control spray which can be delivered by a pump spray which will contain less than 80% alcohol solvent; which will provide cosmetically acceptable curl retention; low tack and drying time; better rinse-out and little or no flaking; high shine (luster); and a crystal clear formulation which yields a clear dried film.

BRIEF SUMMARY OF THE INVENTION

The present invention relates to a composition for a pumpable hair spray which meets standards of alcohol content and still meets the demanding cosmetic requirements for such a product. More particularly, the present invention is based on the remarkable discovery of a hair spray formulation comprising a novel combination of water and alcohol solvent base, essential fixative resins, neutralizing agents, silicone plasticizers and non-essential fragrance and coloring ingredients.

Accordingly, a principal object of the present invention is to provide a novel and unique hair spray product which meets all of the requirements of current clean air legislation without sacrificing those physical properties which today's consumer demands in such products.

Another object of the present invention is to provide a novel hair spray which is dispensable from a hand pump container.

A still further object of the present invention is to provide a novel and unique hair spray which provides equal or better curl retention than that previously obtainable with sprays having essentially a 100% alcohol solvent system.

Still another object of the present invention is to provide a novel and unique pumpable hair spray containing less than 80% alcohol but which provides equal or better tack and drying time than that heretofore obtainable with sprays having essentially a 100% alcohol solvent system.

A still further objective of the present invention is to provide a new and unique hair spray formulation containing approximately 15% water as solvent while obtaining equal or better rinse-out without flaking, and equal or better shine than heretofore obtainable with sprays having a 95–100% alcohol solvent system.

These and still further objects, as shall hereinafter appear, are readily fulfilled by the present invention in a remarkably unexpected manner as will be readily discerned from the following detailed description of an exemplary embodiment thereof.

DESCRIPTION OF THE PREFERRED EMBODIMENT

The present invention comprises a unique mixture of ingredients which yields a remarkably effective and cosmetically pleasing hair spray which is applied from a pump sprayer and based in an environmentally acceptable solvent system.

One motivating factor leading to the present invention is the mandate requiring such products to contain 80% or less alcohol and the determination that there was a lot more to this project than simply pouring more water into the bottle.

In a preferred embodiment, the present invention comprises, by weight percent; water in the range of 8 to 23 percent, alcohol in the range of 75 to 80 percent, fixative resins in the range of 1.5–2 percent, potassium hydroxide (KOH) neutralizer in the range of 0.2–1.72 percent, and silicone plasticizers in the range of 0.2–0.7 percent.

The only resin found to be satisfactory was octylacrylamide/acrylates/butylaminoethyl methacrylate copolymer (herein "OABM"). This material may be used either alone or in combination with one other secondary resin, octylacrylamide/acrylates copolymer (herein "OAA").

Potassium hydroxide (KOH) was the only neutralizing agent found to be effective to neutralize the acid effects of the resins, provided it was blended with the other essential ingredients of this invention. Potassium hydroxide was found to be responsible for lowering the drying time and stickiness time. This helped our invention by countering the negative effects of the addition of water to the formulation. Addition of water makes hair spray tackier and over plasticized which results in a sticky hair feel and slower drying time. See data below (Prepared by Meczka Marketing Research, March 1992)

| | Salon Testing Results | | | | |
|---|---|---|---|---|---|
| TEST PANEL: | Natural Hold Prototype 20 | Super Hold Prototype 19 | Intense Hold Prototype 21 | Vidal Sassoon Extra 20 | Paul Mitchell Freeze & Shine 40 |
| | Drying time versus usual brand used by panelist | | | | |
| Better | 55% | 32% | 62% | 60% | 60% |
| Same | 35% | 47% | 33% | 30% | 28% |
| Worse | 10% | 21% | 5% | 10% | 22% |

Two specific silicone materials are required, these being a blend of polyphenylmethylsiloxane and dimethicone/glycol copolymer.

Although none of these essential ingredients of this composition is unique per se, the combination of ingredients in the specific ranges described herein and set forth below, yields a performance that either matches or exceeds the prior art 100% alcohol based formulations and provide unexpected and surprising results.

The composition of the hair spray of the present invention, in weight percent is:

| INGREDIENT | Range in weight % |
|---|---|
| Alcohol* | 75% to 80% |
| Water | 8% to 23% |
| OABM | 1.9% to 9% |
| OAA | 0% to 3% |
| Potassium Hydroxide | 0.2% to 1.72% |
| Polyphenylmethylsiloxane | 0.1% to 0.3% |
| Dimethicone Glycol copolymer | 0.1% to 0.3% |
| Other ingredients in a quantity sufficient to make 100%. | |

*In practice, the alcohol is added as 190 proof, that is, 95% alcohol with 5% water by volume.

In the practice of the present invention, three formulations providing varying degrees of "hold" power have been accomplished. The compositions hereof contain the following ingredients in the following ranges (expressed in weight percent);

| Ingredient | In weight percent | | |
|---|---|---|---|
| | Intensive Hold | Super Hold | Regular Hold |
| Water | | 8% to 23% | |
| Potassium Hydroxide | | 0.2% to 1.72% | |
| Alcohol | | 75% to 80% | |
| Octylacrylamide/Acrylates/Butyl-aminoethyl methacrylate copolymer | | 1.9% to 9% | |
| Octylacrylamide/Acrylates Copolymer | | 0% to 3% | |
| Polyphenylmethylsiloxane | | 0.1% to 0.4% | |
| Dimethicone/glycol copolymer | | 0.1% to 0.3% | |
| Triethyl citrate | | 0.05% to 0.2% | |
| Other ingreidents quantity sufficient to make 100% | | | |

Extensive laboratory testing was performed to evaluate the efficacy and performance of the present invention. The products were evaluated for hold and curl retention, rinsability/buildup, and hair shine. In addition consumer and independent marketing survey testing evaluated other factors including feel, flaky residue, drying time, and consumer impression. The modes of investigation used include in-vitro, quantitative laboratory studies, in-vivo half head studies and an independently conducted consumer test. Laboratory test results are summarized below, describing the performance of the current invention compared to currently available consumer products where applicable.

Curl Retention—An in-vitro laboratory curl retention study was done to evaluate the effectiveness of three embodiments of the present invention; Intense Hold, Super Hold, and Natural Hold in retaining curl in permed and water set hair at 50% and 90% humidity. Leading competitive brands were evaluated for comparison.

Swatches of European virgin light brown hair were subjected to the methods which included; 1) washing with 1 ml. of Neutrogena Shampoo for Permed and Color Treated Hair and then rinsed under warm tap water, 2) air dried at 40% humidity and 25° C., 3) trimmed to uniform length, 4) measured for length to 0.1 cm., 5) measurements recorded as Ls, and 6) combed. The swatch was then secured at the bottom of a pegboard and subjected to 40% humidity—25° C. (40/25) environment for 24 hours. One hour prior to testing they were removed from the board and laid flat. Samples to be tested for curl retention of permed hair were treated with a commercial alkaline perm solution and allowed to dry, laying flat, at the 40/25 environment for 24 hours.

Five sample swatches were used for each product tested and five additional for control. Testing was performed by spraying each swatch with the selected product, dried (1 hr.), and measured for length (Lo). The environment was maintained at 40/25 throughout the testing period. The swatches were then suspended vertically in a humidity chamber at either 50% or 90%. Measurements of the length of the sample were then made at various times throughout a 24 hour period. Curl retention was calculated using the equation:

$$\% \text{ Curl Retention} = \frac{Ls - Lt}{Ls - Lo} \times 100$$

Where
Ls=initial length after trimming
Lo=length after curling & spraying
Lt=length at various times in chamber Results of the testing performed on the various samples appear in TABLE I-TABLE IV.

TABLE I

Curl Retention of Permed Hair at 90% Humidity

| Product | % Curl Retention and standard deviation | | | |
|---|---|---|---|---|
| | 15 min | 1.5 hours | 2.5 hours | 20 hours |
| NGNA Natural | 97 ± 4 | 87 ± 6 | 84 ± 6 | 85 ± 6 |
| NGNA super | 96 ± 5 | 89 ± 5 | 86 ± 8 | 84 ± 7 |
| NGNA Intense | 96 ± 4 | 90 ± 6 | 89 ± 6 | 93 ± 7 |
| Paul Mitchell | 92 ± 6 | 80 ± 4 | 79 ± 5 | 77 ± 6 |
| Aqua Net Ultimate | 93 ± 4 | 89 ± 4 | 86 ± 7 | 85 ± 6 |
| Vidal Sassoon Extra | 92 ± 2 | 84 ± 3 | 83 ± 3 | 80 ± 5 |
| Pantene Natural | 89 ± 3 | 78 ± 4 | 72 ± 6 | 71 ± 9 |
| Final Net Regular | 85 ± 5 | 72 ± 8 | 63 ± 12 | 61 ± 6 |
| Aqua Net Super | 90 ± 6 | 81 ± 8 | 71 ± 11 | 73 ± 5 |
| Rave Super | 84 ± 7 | 75 ± 6 | 73 ± 6 | 70 ± 10 |
| Rave Ultra | 84 ± 10 | 73 ± 8 | 64 ± 12 | 65 ± 11 |
| Control-Untreated Hair | 79 ± 8 | 70 ± 9 | 68 ± 11 | 63 ± 12 |

TABLE II

Curl Retention of Permed Hair at 50% Humidity

| Product | % Curl Retention and standard deviation | | | |
|---|---|---|---|---|
| | 30 min | 1.5 hours | 2.5 hours | 18 hours |
| NGNA Natural | 98 ± 2 | 97 ± 3 | 96 ± 2 | 95 ± 2 |
| NGNA Super | 97 ± 3 | 96 ± 2 | 94 ± 3 | 93 ± 4 |
| NGNA Intense | 98 ± 3 | 97 ± 3 | 97 ± 3 | 97 ± 4 |
| Paul Mitchell | 99 ± 2 | 95 ± 2 | 95 ± 5 | 94 ± 5 |
| Aqua Net Ultimate | 99 ± 1 | 97 ± 3 | 94 ± 4 | 93 ± 4 |
| Vidal Sassoon Extra | 97 ± 4 | 97 ± 4 | 93 ± 4 | 90 ± 5 |
| Control-Untreated Hair | 96 ± 4 | 92 ± 4 | 90 ± 4 | 87 ± 3 |

TABLE III

Curl Retention of Wet Set Virgin Hair at 90% Humidity

| Product | % Curl retention and standard deviation | | | |
|---|---|---|---|---|
| | 1 Hour | 3 hours | 6 hours | 24 hours |
| NGNA Natural | 34 ± 4 | 40 ± 9 | 32 ± 4 | 32 ± 5 |
| NGNA Super | 50 ± 6 | 43 ± 9 | 46 ± 10 | 43 ± 6 |
| NGNA Intense | 39 ± 6 | 36 ± 8 | 35 ± 6 | 37 ± 7 |
| Paul Mitchell | 38 ± 11 | 23 ± 3 | 25 ± 3 | 21 ± 3 |
| Aqua Net Ultimate | 21 ± 6 | 17 ± 3 | 16 ± 4 | 15 ± 6 |
| Vidal Sassoon Extra | 31 ± 7 | 27 ± 6 | 26 ± 6 | 27 ± 5 |
| Final Net Regular | 13 ± 4 | 7 ± 4 | 5 ± 3 | 5 ± 3 |
| Control-Untreated | 4 ± 4 | 0.3 ± 0.7 | 0 | 0 |

TABLE III-continued

Curl Retention of Wet Set Virgin Hair at 90% Humidity

| Product | % Curl retention and standard deviation | | | |
|---|---|---|---|---|
| Hair | 1 Hour | 3 hours | 6 hours | 24 hours |

TABLE IV

Curl Retention of Wet Set Virgin Hair at 50% Humidity

| Product | Curl retention and standard deviation | | |
|---|---|---|---|
|  | 1 Hour | 2 Hours | 18 Hours |
| NGNA Natural | 54 ± 7 | 51 ± 8 | 46 ± 7 |
| NGNA Super | 70 ± 7 | 68 ± 7 | 63 ± 8 |
| NGNA Intense | 75 ± 8 | 72 ± 10 | 71 ± 9 |
| Paul Mitchell | 68 ± 8 | 66 ± 6 | 64 ± 6 |
| Aqua Net Ultimate | 46 ± 15 | 42 ± 15 | 35 ± 13 |
| Vidal Sassoon Extra | 60 ± 7 | 53 ± 6 | 48 ± 6 |
| Control-Untreated Hair | 31 ± 6 | 26 ± 5 | 20 ± 6 |

Swatches were prepared using 2.5±0.05 g European virgin dark brown hair (De Meo Bros. New York, New York) allowing use of 20 cm. of the hair. The swatches were prewashed with 1 ml. of Neutrogena shampoo for permed and color treated hair, rinsed for 1 min. with warm tap water (38° C.) and dried in a controlled humidity and temperature environment of 40%±5% RH and 20° C.±2° C. for a minimum of 24 hours or until at constant weight. Any loose hairs were pulled from the swatches and then they were weighed on an analytical balance to the nearest 0.0001 gram and the weight recorded. The temperature and humidity of the room were recorded at each weighing. The swatches were divided into groups of five per test product and two untreated control groups. An environmental control group was used to monitor and correct for any changes in humidity which would affect the weight of the hair. A second control group was used to monitor any change in weight as a result of the wash procedure.

One milliliter of the test product was applied to each swatch in the respective test group with a 1 ml. disposable syringe. The hair spray was applied evenly and carefully along the length of the swatch so as not to let any product drip off the swatch. The treated swatches were hung vertically to dry at 40% RH and 22° C. When completely dry they were weighed and the weight recorded. When at constant weight the swatches were wetted with warm tap water (38° C.) until the hair was saturated and then washed with 2 ml. of Neutrogena R Shampoo for Permed and Color Treated hair for 1 minute and then rinsed for another minute under tap water at 38° C. and 2000-2500 cc./min. Each swatch was washed in the same manner and then hung to dry overnight at 40% RH and 22° C. When completely dry and at constant weight the swatches' weight was recorded and the weight of any residue calculated as a percent of the amount of product applied. To determine if buildup would occur, the swatches were again treated with the respective test product and the same procedure followed.

The hair spray test products were: Aqua Net ® Ultimate hold, Neutrogena ® Natural hold (506-66AV), Neutrogena ® Super hold (506-65AV), Neutrogena ® Intense hold (506-72), Paul Mitchell ® Freeze and Shine and Vidal Sassoon ® Extra hold.

TABLE V, below, shows the results from the in vitro quantitative laboratory study. The data is presented as the per cent of hair spray residue remaining on the hair after washing with shampoo. All of the products tested were removed over 90 percent. Natural hold, Super hold and Intense hold hair sprays were over 95% removed with one shampoo, therefore leaving virtually no residue.

TABLE V

Laboratory Rinsability/Buildup Results
% Hairspray residue left on hair after shampooing

| PRODUCT | % Residue & SD* 1 Treatment | % Residue & SD* 2 Treatments |
|---|---|---|
| NGNA Natural | 2.5 ± 2.1 | −0.5 ± 0.8 |
| NGNA Super | 3.9 ± 3.3 | 1.4 ± 2.2 |
| NGNA Intense | 1.7 ± 0.9 | 0.08 ± 1.2 |
| Paul Mitchell | 7.7 ± 2.5 | 3.7 ± 1.3 |
| Aqua Net Ultimate | 6.9 ± 3.8 | 7.6 ± 1.8 |
| Vidal Sassoon Extra | 3.7 ± 5.9 | 1.1 ± 4.2 |

*SD is standard deviation

From the foregoing it is apparent that a hair spray has been herein described and illustrated which fulfills all of the aforestated objectives in a remarkably unexpected fashion. It is of course understood that such modifications, alterations and adaptations as may readily occur to the artisan confronted with this disclosure are intended within the spirit of this disclosure which is limited only by the scope of the claims appended herein.

Accordingly, what is claimed is:

1. A crystal clear hand pumpable hair spray composition comprising, in weight percent: from about 75 to about 80 percent of alcohol; from about eight to about 23 percent water; from about 1.9 to about 9 percent of a fixative resin selected from the group consisting of octylacrylamide/acrylates/butylaminoethyl methacrylate copolymer, octylacrylamide/acrylates copolymer or a mixture thereof; from about 0.2 to about 0.7 percent of silicone plasticizer; in which said silicone plasticizer consist of a blend of polyphenymethyl siloxane and diomethicone/glycol copolymer in a ratio of about 1:3 to about 4:1 respectively; from about 0.2 to about 1.72 percent of potassium hydroxide neutralizer, said resin, said silicone plasticizer and said potassium hydroxide being dispsered throughout said water and said alcohol.

* * * * *